United States Patent [19]

Perdriat

[11] Patent Number: 4,919,646
[45] Date of Patent: Apr. 24, 1990

[54] SYSTEM FOR AUTOMATICALLY BALANCING A CENTRIFUGE IN OPERATION

[75] Inventor: Jacques Perdriat, Maule, France

[73] Assignee: Acutronic France, Les Clayes-Sous-Bois, France

[21] Appl. No.: 297,060

[22] Filed: Jan. 13, 1989

[30] Foreign Application Priority Data

Jan. 18, 1988 [FR] France .................. 88 00506

[51] Int. Cl.$^5$ .............................. B04B 9/14
[52] U.S. Cl. ........................... 494/1; 494/10; 494/19; 494/31; 494/82
[58] Field of Search ................ 494/1, 5, 7, 10, 11, 494/19, 20, 27, 31, 33, 37, 82, 84, 902; 422/72, 100, 102; 436/45; 74/573 F

[56] References Cited

U.S. PATENT DOCUMENTS

| | | | |
|---|---|---|---|
| 4,096,988 | 6/1978 | Scuricini | 494/7 |
| 4,099,667 | 7/1978 | Uchida | 494/82 |
| 4,157,781 | 6/1979 | Maruyama | 494/7 |
| 4,295,386 | 10/1981 | Zhivotov | 74/573 F |
| 4,433,592 | 2/1984 | Tatsumi et al. | 74/573 F |
| 4,537,177 | 8/1985 | Steere, Jr. et al. | 74/573 F |
| 4,671,940 | 6/1987 | Holen et al. | 494/19 |
| 4,700,117 | 10/1987 | Giebeler et al. | 494/7 |

OTHER PUBLICATIONS

1984 SID International Symposium Digest of Technical Papers, pp. 120–123, article by J. Eyth, Jr., entitled "8.4: A CGI Simulation Display in a High-G Environment".

Primary Examiner—Timothy F. Simone
Attorney, Agent, or Firm—Webb, Burden, Ziesenheim & Webb

[57] ABSTRACT

The system for automatically balancing a centrifuge in operation comprises a system for selectively displacing a mass of fluid inside at least one hollow horizontal tube (25) incorporated in the rotary arm (20), together with an unbalance measuring circuit (7 to 14) for the rotary arm (20) which may be out of balance. The unbalance measuring circuit (7 to 14) includes sensors (7) preferably disposed on the stand (23) of the centrifuge, circuits (8 to 14) for processing the signals delivered by the sensors in order to deliver alarm signals or signals for controlling rebalancing in the event that an unbalance is detected, and control means (4) for controlling said system for selectively displacing a mass of fluid, said control means responding to the rebalancing control signals delivered by the unbalance measuring circuit (8 to 14) in order to give rise to selective displacement in real time of a mass of liquid fluid inside said hollow horizontal tube (25), preferably in conjunction with the displacement of a free piston (6), thereby dynamically balancing the rotating arm (20) of the centrifuge.

13 Claims, 6 Drawing Sheets

SYSTEM FOR AUTOMATICALLY BALANCING A CENTRIFUGE IN OPERATION

The present invention relates to a system for automatically balancing a centrifuge in operation, the centrigue comprising a rotary arm including at least one horizontal tube mounted on a turret and rotated about a vertical axis relative to a stand.

BACKGROUND OF THE INVENTION

Centrifuges are used in numerous fields, and in particular as geotechnical centrifuges for research or industrial work. In such cases, a centrifuge is used to simulate stresses to which structures may be subjected, e.g. under the effect of earthquakes, and various amounts of data are taken from tests performed on a model or prototype at reduced scale which is placed in a swinging basket suspended at the end of the rotary arm of the centrifuge. During testing in which model structures are subjected to forces which increase or alternate by virtue of the rotary arm of the centrifuge being rotated at different speeds of rotation or in alternating cycles, various measurements are performed on the scale model structures in order to design mathematical models representative of the behavior of the structures.

Testing often continues until the structure placed in the basket of the centrifuge collapses. This gives rise suddenly to a major unbalance in the centrifuge. In order to rebalance the centrifuge after the model has collapsed, it is necessary to stop the centrifuge in order to act on the mass or the location of the counterweights which are generally place on the oppostie end of the rotary arm to the basket containing the model being subjected to mechanical strength testing. Such rebalancing operations take a long time. Sometimes, the sudden unbalance generated by a model collapsing can even damage the centrifuge, thereby delaying further testing. It may also be observed that major unbalance can occur during testing even though a model under test has not collapsed. This happens, for example, when testing structures that co-operate with fluctuating masses of liquid, e.g. when testing dam or dyke structures.

The present invention seeks to remedy the above-mentioned drawbacks and to make it possible to detect and automatically compensate an unbalance that may appear in a centrifuge in operation in a manner which is simple and effective and which does not require the centrifuge to be stopped.

SUMMARY OF THE INVENTION

These objects are achieved by means of a system for automatically balancing a centrifuge in operation, the centrifuge including a rotary arm including at least one horizontal tube mounted on a turret for rotation about a vertical axis relative to a stand, said balancing system comprising a system for selectively displacing a mass of fluid inside said hollow horizontal tube, and a circuit for measuring any unbalance of the rotary arm which may be out-of-balance, and the circuit for measuring the unbalance comprising sensors disposed on the centrifuge, circuits for processing the signals or rebalancing control signals in the event of unbalance being detected, and control means for controlling said system for selectively displacing a mass of fluid, said contorl means responding to rebalancing control signals delivered by the unbalance measuring circuit in order to give rise to selective real time displacement inside said hollow horizontal tube of a mass of fluid for dynamically rebalancing the rotating arm of the centrifuge.

More particularly, the sensors comprise four strain-gauge bridges disposed on elastically deformable parts incorporated in the stand or in the connections between the stand and its foundation, with the four strain gauges lying in a horizontal plane at equal distances from the vertical axis of rotation of the rotary arm and being diametrically opposed in pairs along two mutually orthogonal directions.

Advantageously, the unbalance measuring circuit comprises a signal-shaping circuit for shaping the signals delivered by the strain-gauge bridges, a set of four pairs of sample-and-hold circuits connected so as to store the voltage maxima and the voltage minima delivered by each of the circuits for shaping the signals delivered by the four strain-gauge bridges, four first two-input summing circuits each connected to receive the signals delivered by a pair of sample-and-hold circuits recording the voltage maximum and the voltage minimum from a respective one of the signal-shaping circuits, each of said summing circuits determining the absolute value of the difference between the voltage maximum and the voltage minimum applied thereto, a first four-input summing circuit connected to receive the signals from said first four two-input summing circuits, and circuits for using the signals delivered by the first four-input summing circuit in order to deliver signals representative of the level of unbalance in the rotating arm to a display member and to members for controlling the system for selectively displacing a mass of fluid inside said hollow horizontal tube in order to reduce the level of unbalance in the rotating arm, when necessary.

In a first embodiment of the invention, the system for selectively displacing a mass of fluid inside said hollow horizontal tube comprises an actuator having a free piston with two transverse end faces delimiting two end chambers inside the hollow cylinder, filling means for filling the empty space situated between the transverse end faces of the free cylinder and the end chambers with oil, an oil tank together with a hydraulic pump, and an oil-removing circuit for removing the oil situated in one or other of the end chambers, said oil-removing circuit being provided with servo-valves under the control of control signals generated by the unbalance measuring circuit.

In a second embodiment of the invention, the system for selectively displacing a mass of fluid inside the hollow horizontal tube comprises a pair of flexible membranes disposed inside the hollow tube and connected in fluid-tight manner to the side wall of the horizontal tube in two radial planes at respective distances from the ends of said tube, means for filling the empty space between the membranes with a liquid fluid, a device for providing a gaseous fluid under pressure, and a selective connection circuit between said device for supplying a gaseous fluid under pressure and each of the variable volume chambers situated between the flexible membranes and the corresponding ends of the hollow tube, said selective connection circuit including servo-valves controlled by control signals delivered by the unbalance measuring circuit.

In another embodiment of the invention, the system for selectively displacing a mass of fluid inside the hollow horizontal tube comprises a first chamber and a second chamber delimited by fixed walls and separated from each other by a fixed transverse wall which includes the axis of rotation of the turret, means for filling one of the chambers with a liquid fluid, ducts for putting the two chambers into communication with each other, a device for providing a gaseous fluid under pressure, and a selective connection circuit between the device for providing the gaseous fluid under pressure and each of the chambers, said selective connection circuit including servo-valves controlled by control signals delivered by the unbalance measuring circuit.

Advantageously, the control of the system for selectively displacing a mass of fluid inside the hollow horizontal tube is capable of being disengaged from the unbalance measuring circuit when the rotary arm of the centrifuge is rotating at a low speed, with the balancing mass being maintained in a neutral position.

The invention also provides a centrifuge comprising a rotary arm constituted by two parallel tubes each of which is equipped with a system for selectively displacing a mass of fluid inside the bore of the corresponding tube, with each of the systems for selectively displacing a mass of fluid being controlled from a common unbalance measuring circuit.

BRIEF DESCRIPTION OF THE DRAWINGS

Embodiments of the invention are described by way of example with reference to the accompanying drawings, in which.

MORE DETAILED DESCRIPTION

Figure 2:
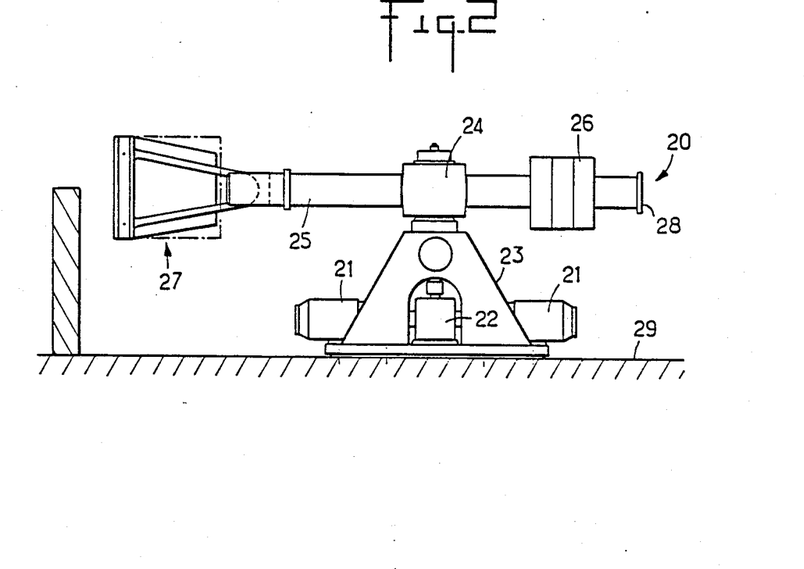
FIGS. 2 and 3 are respectively an elevation view and a plan view of an example of a geotechnical centrifuge to which the invention is applicable.
Figure 3:
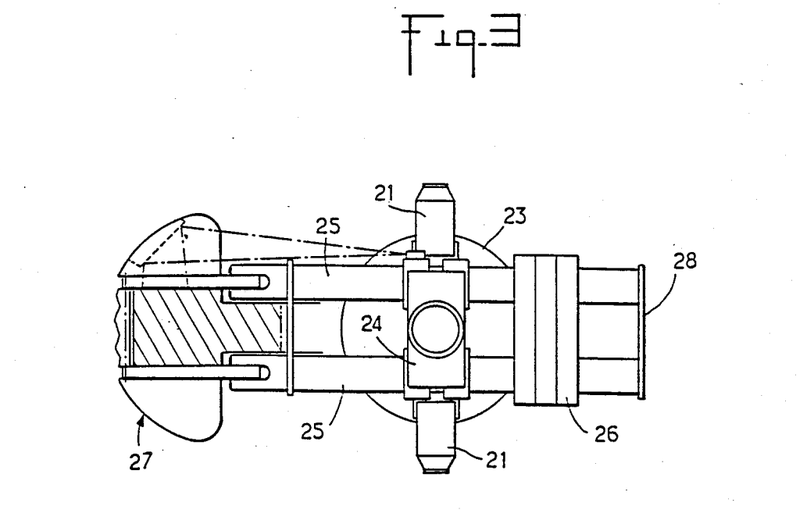

FIGS. 2 and 3 show a centrifuge which is particularly adapted to geotechnical applications and to which the invention is applicable.

In conventional manner, such a centrifuge comprises a stand 23 which is advantageously in the form of a pyramid or a truncated cone and which has its base anchored to foundations 29. Electric motors 21 co-operate with a stepdown gear box 22 in order to rotate a turret 24 on which a rotary arm 20 is mounted, with one end of the arm being suitable for having a swinging basket 27 fitted thereto, while that portion of the rotary arm 20 which is situated on the other side of the turret from the basket 27 carries counterweights 26. As shown in FIG. 3, the rotary arm comprises at least one (and preferably two) bored tubes 25 closed at their ends. Each steel tube 25 has a bore extending nearly to its end carrying the basket 27 (FIG. 1) and closed at the end opposite to the basket by a plate 28.

Figure 1:
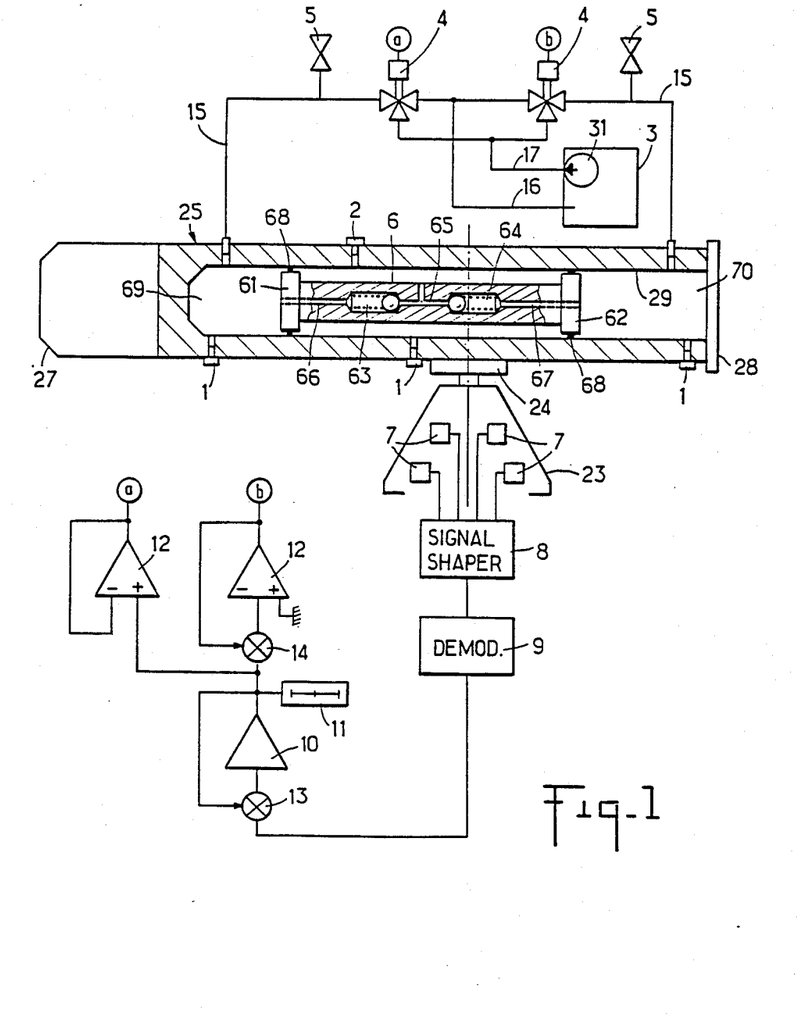
FIG. 1 is a diagrammatic axial section through the rotary arm of a centrifuge equipped with a first embodiment of an automatic balancing system in accordance with the invention.

A first embodiment of the automatic balancing system in accordance with the invention is shown in FIG. 1 which is an axial section through a tube 25 of the rotary arm 20. The hollow horizontal tube 25 which is mounted on the turret 24 and which carries the swinging basket 27 at one of its ends defines a rectified cylinder 29 slidably receiving a free piston 6 having two transverse end facings 61 and 62 delimiting two end chambers 69 and 70 inside the cylinder 29 respectively in conjunction with the end of the tube carrying the basket 27 and with the closure plate 28.

The piston 6 has a central portion of smaller cross section than its transverse end faces 61 and 62 in order to define, in conjunction with the cylinder 29, an annular empty space.

Prior to being used, oil is inserted via an orifice 2 into the annular psace situated betwen the piston 6 and the cylinder 29. Channels 66 and 67 including non-return valves 63 and 64 are provided inside the piston 6 and put the annular space lying between the piston 6 and the cylinder 29 into communication with each of the end chambers 69 and 70 while the annular space is being filled with oil. Once oil filling has been completed, the orifice 2 is closed and the non-return valves 63 and 64 prevent any fluid from returning from the end chambers 69 and 70 towards the central annular space provided between the piston 6 and the cylinder 29. The end faces 61 and 62 of the piston 6 are provided with piston rings 68, but is should be observed that there is no need for perfect sealing around the end faces 61 and 62.

Purge means 1 are disposed in the bottom portion of the wall of the hollow tube 25 in order to enable each of the end chambers 69 and 70 to be purged together with the central annular space.

An oil tank 3 and a hydraulic pump 31 capable of generating pressures of about $200 \cdot 10^5$ Pa, for example are connected respectively via a line 17 and a return line 16 to two 5/2 type proportional action servo-valves 4 controlled by control signals generated by the unbalance measuring circuit described below. Each of the servo-valves 4 is connected to a respective one of the end chambers 69 and 70 via a line 15.

2/2 type valves 5 are disposed on each of the lines 15 for venting and removing an oil, such that the purge means 1 could be omitted, if necessary.

The system shown in FIG. 1 provides automatic balancing by displacing a free piston 6 constituted by a heavy mass of steel inside each of the hollow tubes 25. Since each of the hollow tubes 25 is completely filled with oil apart from the volume occupied by the piston 6 per se, as described above, each piston 5 is displaced by hydraulic action controlled by the two proportional action servo-valves 4 which in turn respond to control signals delivered by the circut for measuring unbalance and for generating error signals enabling the unbalance to be automatically compensated by controlling displacement of the compensating piston 6. Any change in the position of the center of gravity of the load can thus be compensated automatically.

The hydraulic pump 31, the oil tank 3 and the servo-valves 4 are disposed in the central portion of the rotary arm 20 of the centrifuge in a zone subjected to little stress, and they do not interfere with the operation of the centrifuge.

The balancing system of the invention can compensate unbalance over a very wide range of values, about ±20,000 N, in a very limited reaction time, about 2 minutes, and return to initial balance. The accuracy of the balancing system is also very high since at accelerations of about ten times the value g, an unbalance of ±1 kg can be detected.

Mangentic type detectors may be used to center the piston when stationary.

As already mentioned, each of two parallel hollow tubes 25 may be fitted with a system for selectively displacing a mass of fluid inside the corresponding tube, e.g. the piston hydraulic system described above, with each of the selective displacement systems being controlled by a common circuit for measuring unbalance. However, it is also possible, when using two parallel tubes 25 each of which is equipped with a system for compensating unbalance, to combine the compensating actions in a special manner, e.g. in order to displace the center of mass into a plane lying outside the axis of rotation of the machine.

Further, although the body of this description relates in general manner to the case of a balancing system which is used on a permanent basis to compensate unbalance as it occurs, there are some special applications in which the control of the means for selectively displacing the fluid, and thus the piston 6, inside a hollow horizontal tube 25 may be disengaged from the unbalance measuring circuit when the rotary arm 20 of the centrifuge is rotating slowly. Unbalance changes with speed of rotation and it is preferable for the counterweights 26 (FIGS. 2 and 3) to be positioned in such a manner as to provide balance at those speeds of rotation which give the highest accelerations. Thus, in a particular application, the system for compensating unbalance is disengaged e.g. up to accelerations of about 10 g, and the small amount of unbalance then detected by the circuit or measuring unbalance makes it possible to determine whether the counterweights are properly positioned for achieving balance at speeds of rotation corresponding to higher working accelerations, e.g. about 100 g.

The unbalance measuring circuit includes sensors which may be of the accelerometer type or of the capacitor type, for example, providing signals which are suitable, after processing, for deliverying alarm signals or for controlling rebalancing in the event of unbalance being detected. The servo-valves 4 controlling the selective displacement of the hydraulic fluid respond to rebalancing control signals delivered by the measuring circuit in order to cause selective displacement of the hydraulic fluid to take place in real time inside the, or each, hollow tube 25 in a direction such that it tends to return the rotary arm of the centrifuge to dynamic equilibrium.

Figure 4:
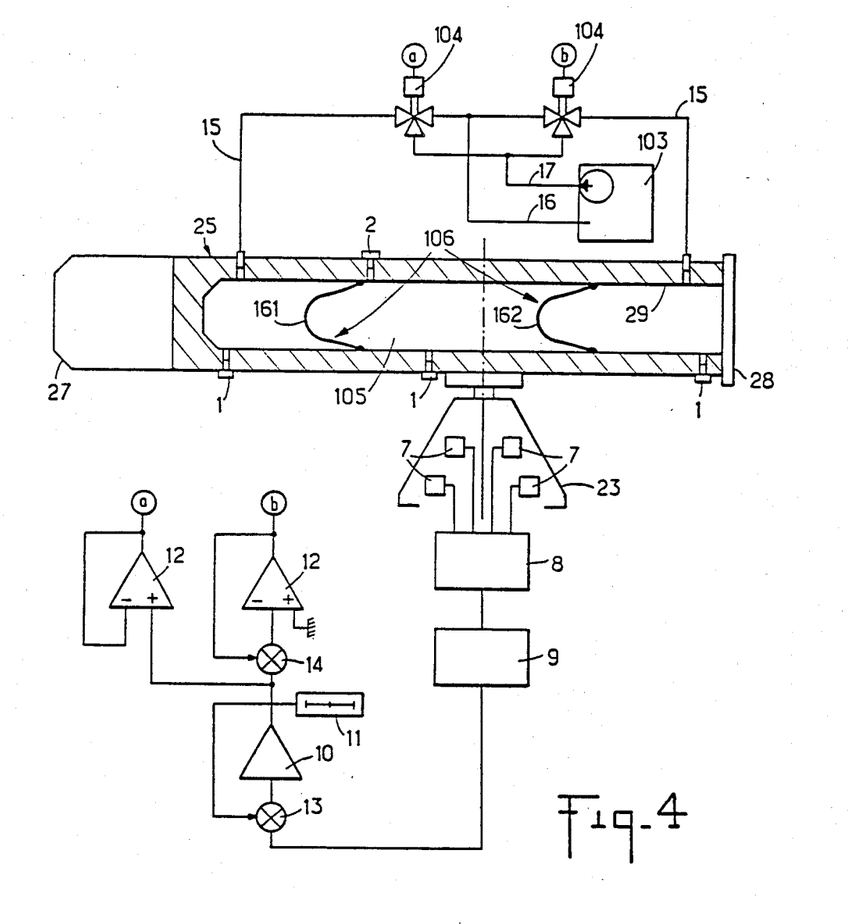
FIGS. 4 and 5 are views similar to FIG. 1 showing centrifuges fitted with automatic balancing systems in accordance with second and third embodiments respectively of the invention.
Figure 5:
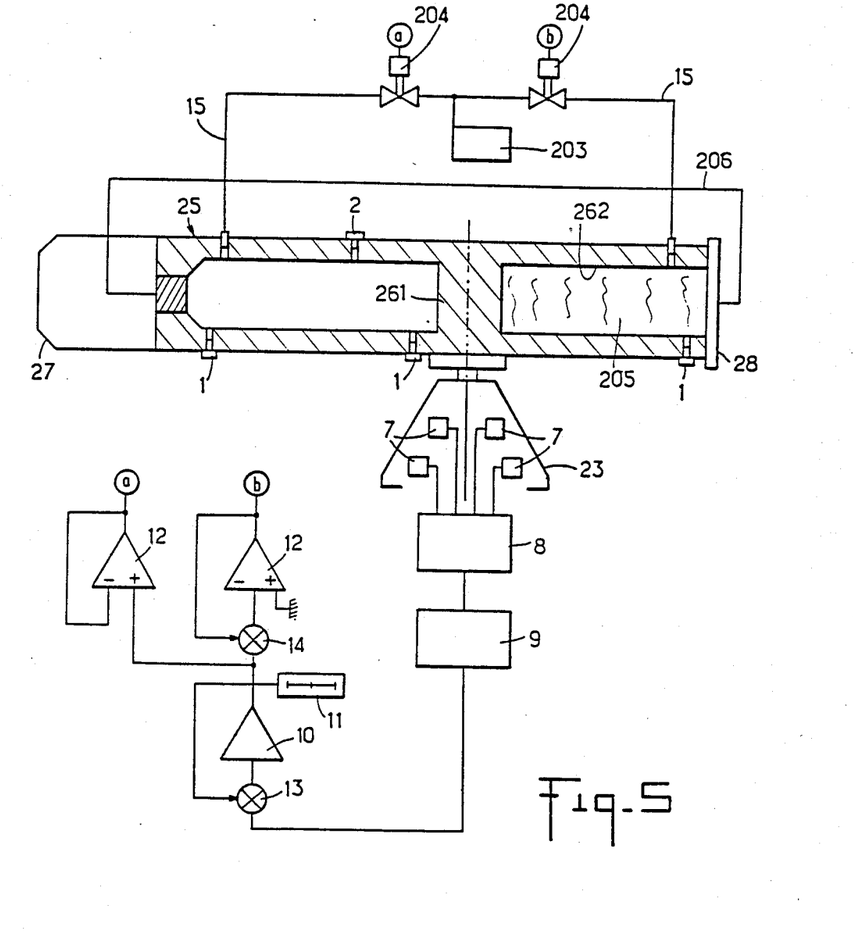

In a preferred embodiment shown in FIGS. 1, 4, and 5, the sensors of the unbalance measuring circuit comprise four strain-gauge bridges disposed on elastically deformable parts incorporated in the stand 23 or in the connection between the stand 23 and its foundation 29. The four strain-gauge bridges 7 are disposed in a horizontal plane at equal distances from the vertical axis of rotation of the rotary arm 20 and they are diametrically opposite each other in pairs along two mutually orthogonal directions. The positions of the four strain gauges 7 are referenced by the letters A, B, C, and D in FIG. 7.

The implementation of this type of sensor is described below.

Even if it is fitted with a swinging basket, the rotating arm of a centrifuge has the special feature of having its mass concentrated in a volume of small vertical extent, and this may be approximated by a plane.

The arm is built symmetrically and its mass is greater than the mass of the payload so the center of the combined mass is located on the axis of symmetry of the arm or very close thereto, regardless of the position of the center of mass of the payload.

The circuit for measuring unbalance by means of strain gauges located in a plane, and the associated balancing system, take these features into account, while nevertheless retaining the possibility of being applicable to more complex cases.

The forces generated by an unbalance alternate at a frequency equal to the speed of rotation of the machine and are transmitted to the foundation to which the machine is fixed via its stand 23.

These forces are measured by the four strain-gauge bridges 7 disposed at 90° intervals on elastically deformable parts integrated in the stand 23 or in the connections between the stand and the foundation.

An unbalanced arm rotating at constant speed generates forces in the frame 23 which are sinusoidal.

The phases of said sinusoidal forces relative to the references axes of the stand depend on the instantaneous position of the unbalance relative to the stand, and consequently on the position of the rotating arm.

Figure 7:
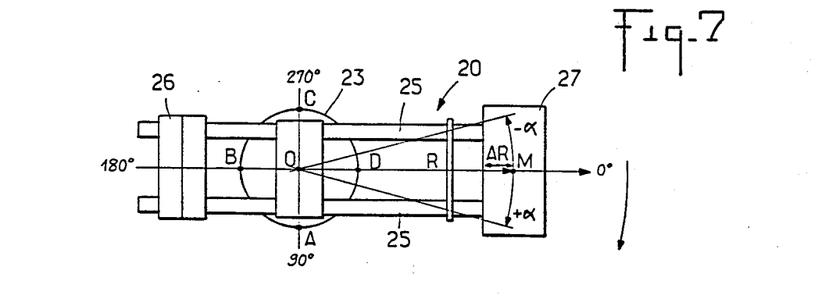
FIG. 7 is a plan view of a centrifuge fitted with a circuit for detecting unbalance in accordance with the invention and showing the positions of the various sensors whose output signals are shown in the diagrams of FIGS. 6A to 6D.

In FIG. 7, the rotating arm 20 comprising two hollow tubes 25 is shown in its origin position with the axis of the arm 20 passing through the center of rotation O and the center of mass M of the basket 27 coinciding with the axis from which annular positions are measured. The points A, B, C, and D are situated on the stand 23 at angular positions of 90°, 180°, 270°, and 0° respectively and represent the geometrical positions of the strain gauges 7.

The waveforms of the voltage signals delivered by the bridges 7 situated at points A, B, C, and D are shown by curves A, B, C, and D in FIGS. 6A, 6B, 6C, and 6D as a function of the angular position $\theta$ of the rotary arm 20, and thus as a function of time.

Figure 6A:
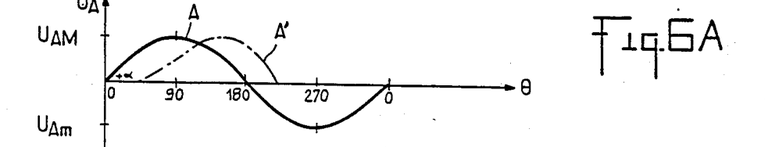
FIGS. 6A and 6D are waveform diagrams showing changes in the output signals form the sensors of the circuit for detecting unbalance as a function of the angular position of the rotary arm of the centrifuge.

In the presence of unbalance, if the center of mass M situated on the longitudinal axis of the rotating arm 20 is displaced on a circle of radius R (FIG. 7) through an angle $+\alpha$ or $-\alpha$, then the phase of the forces generated by the unbalance is also offset through a corresponding angle $+\alpha$ or $-\alpha$. This is illustrated in FIG. 6A by curve A'.

Figure 6B:
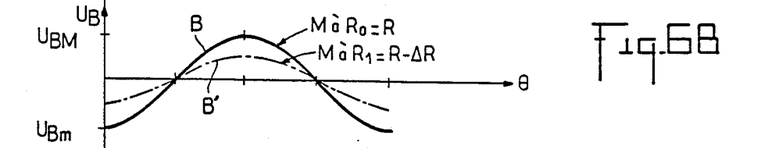
Figure 6C:
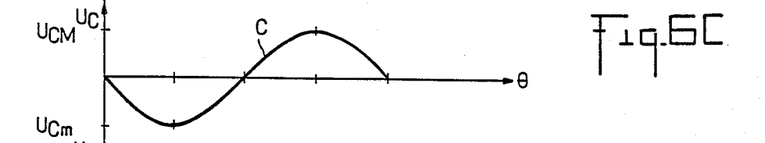
Figure 6D:
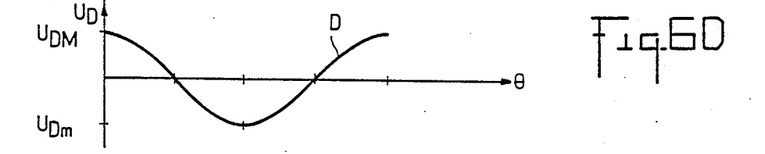

If the center of mass M is displaced relative to the center of rotation O by $+\Delta R$ or by $-\Delta-R$, the maximum amplitude measured is changed by $(R+\Delta R)/R$ or by $(R-\Delta R)/R$, as shown by curve B' in FIG. 6B.

The electrical signals provided by the strain gauges 7 (after amplification) are proportional to and in phase with the forces due to the unbalance.

However, other forces may also have an effect on the output voltages delivered by the strain measuring system, in particular expansion and contraction forces.

If no temperture compensation is provided, then an expansion gives rise to a D.C. signal being superimposed on the measured A.C. signal.

Other phenomena such as long term drift in the amplifiers also give rise to the addition of a D. C. voltage.

Figure 8:
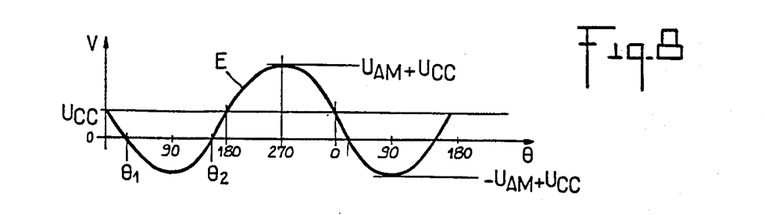
FIG. 8 is a waveform diagram analogous to FIG. 6A but corresponding to a situation which includes interfering phenomena of expansion or drift.

FIG. 8 shows a waveform E representative of the output voltage from strain-gauge bridge A after translation by such a D.C. offset.

Examination of this offset waveform shows that:

(a) the zero crossings of the curve no longer correspond to the geometric points 0°, 180°, 360°, etc.;

(b) the peak-to-peak amplitude difference remains constant and equal to:

$$|U_{AM}+U_{CC}-(-I_{AM}+U_{CC}) = 2U_{AM}|$$

(c) the real phase of the signal can be recalculated directly from the phase shift values $\theta_1$ and $\theta_2$ corresponding to its zero crossings.

The measuring circuit associated with the sensors 7 is shown diagrammatically in FIGS. 1, 4, and 5 in the form of a signal-shaping module 8, a demodulation module 9, an amplifier stage 10, a display 11 for displaying the measured unbalance, and amplifiers 12 which deliver error signals a and b to the servo-valves 4 in order to control the operation of the unbalance compensating system, i.e. in order to displace hydraulic fluid form one end chamber 69 or 70 to the other 70 or 69. In FIGS. 1, 4, and 5, references 13 and 14 designated summing circuits for applying feedback signals.

Figure 9:
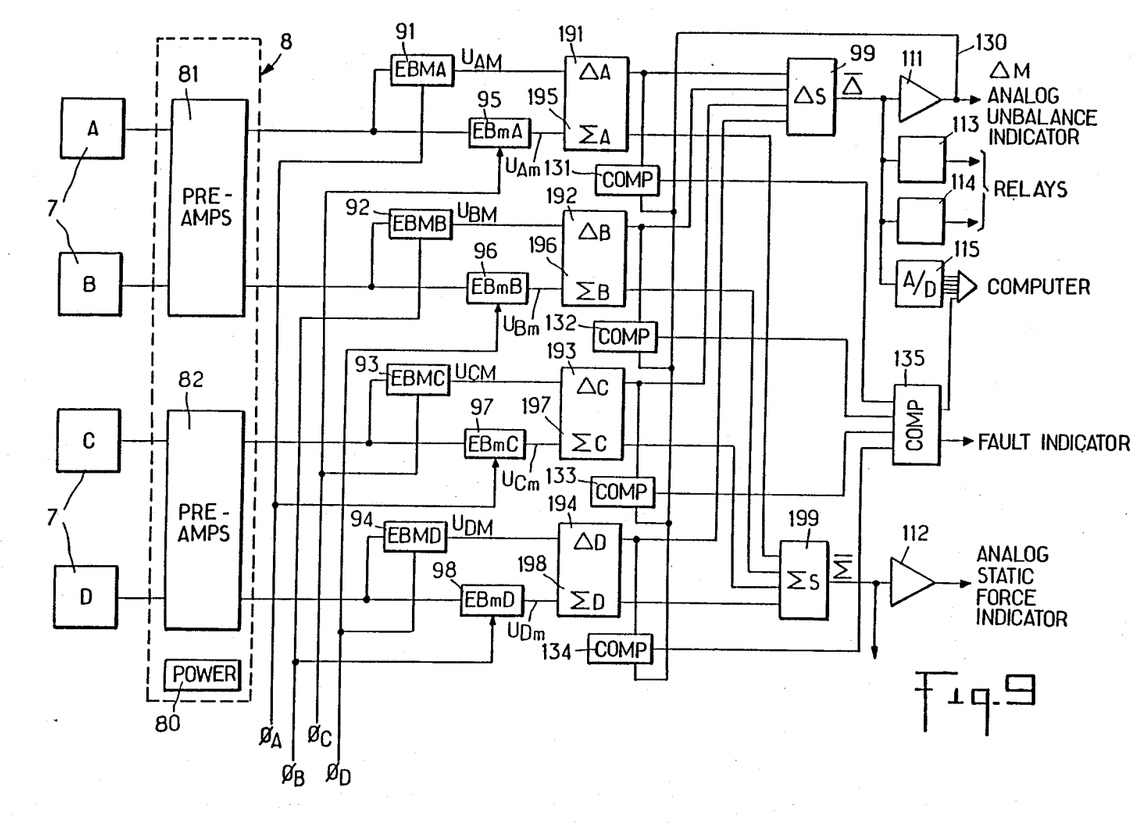
FIG. 9 is a block diagram showing one example of a circuit in accordance with the invention for detecting unbalance.

FIG. 9 is a more detailed view of an embodiment of the unbalance measuring circuit associated with the sensors 7.

The FIG. 9 measuring circuit includes a circuit 8 for shaping the signals from the strain-gauge bridges 7. The circuit 8 provides dynamic shaping and is provided with a power supply 80. It includes two pairs 81 and 82 of preamplifiers with zero compensation situated close to the strain gauges 7. Four pairs of sample-and-hold circuits 81, 85; 92, 96; 93, 97; and 94, 98 are provided for recording the maxima and the minima of the voltages delivered by each of the shaping circuits associated with the strain-gauge bridges 7. The sample-and-hold circuits are controlled by on/off signals generated by the system for encoding the position of the rotary arm 20. These four signals $\phi A$, $\phi B$, $\phi C$, and $\phi D$ are at 90° intervals from one another and are disposed in such a manner that the sample-and-hold circuits store the maxima and the minima in the voltages from the amplifiers 81 and 82.

Four two-input summing circuits 191 to 194 each receive signals from a corresponding pair of sample-and-hold circuits, 91 & 95; 92 & 96; 93 & 97; and 94 & 98 for storing a voltage maximum and a voltage minimum from respective ones of the shaping circuits, and the summing circuits deliver signals corresponding to the absolute values of the differences between said voltage maxima and minima, designated by $\Delta A$, $\Delta B$, $\Delta C$, and $\Delta D$ for the sensors situated at points A, B, C, and D in FIG. 7.

A four-input summing circuit 99 receives these signals from the four two-input summing circuits 191 to 193 and determines the mean value $\Delta$ of the differences $\Delta A$, $\Delta B$, $\Delta C$, and $\Delta D$ constituted by the signals from the two-input summing circuits 191 to 194.

A plurality of circuits 111, 113, 114, and 115 uses the mean value signals $\overline{\Delta}$ from the four-input summing circuit 99 in order to deliver information representative of the amount of unbalance in the rotating arm to display means and to the servo-valves 4 for controlling the system for selectively displacing a mass of fluid inside a hollow horizontal tube 25 in order to reduce the level of unbalance in the rotating arm 20 of the centrifuge, should that be necessary.

The circuit 111 constitutes an amplifier chain suitable for connecting to a display member constituting an analog indicator of a dynamic unbalance. The signals from the amplifier chain 111 may be used on a line 130 to monitor balancing system performance in a manner described below.

The inputs of threshold circuits 113 and 114 are connected to the output form the summing circuit 99 for the purpose of determining two unbalance levels beyond which relays (not shown in the drawing) are used to generate an alarm or to control the servo-valves 4.

The circuit 115 is constituted by an analog-to-digital converter which converts the measured values into digital form for display on a digital type of display and to enable the results of the measurements to be processed by a computer associated with the measuring and rebalance controlling circuit.

The unbalance measuring circuit also includes four comparator circuits 131 and 134 disposed between the output from the four-input summing circuit 99 and respective ones of the inputs to said summing circuit 99. The outputs form the comparator circuits 131 to 134 are connected to a fault-detecting threshold circuit 135 which delivers a signal representative of a fault when the output signal from any one of the comparators 131 to 134 exceeds a predetermined value, e.g. if the difference between the output voltage from one of the chains relative to the average value exceeds 10% of the average, which corresponds to a fault in one of the measurement chains. It is thus possible to trigger an alarm in the event of one of the strain-gauge bridges failing or one of the amplifier chains failing. This security measure is very important in a centrifuge where failure to detect a real unbalance can have disastrous consequences.

The above-described unbalanced measuring circuit eliminates temperature drift and static errors. However, it is often convenient to know the static force being applied to the stand.

To do this, the unbalance meaning circuit includes four second two-input summing circuits 195 to 198 each receiving the signals from a corresponding pair of the sample-and-hold circuits 91 & 95; 92 & 96; 93 & 97; or 94 & 98 used for recording a voltage maximum and a voltage minimum corresponding to a respective one of the shaping circuits ($U_{AM}$ & $U_{AM}$; $U_{BM}$ & $U_{Bm}$; $U_{CM}$ & $U_{Cm}$; $U_{DM}$ & $U_{Dm}$). Each of these summing circuits 195 to 198 determines a respective sum $\Sigma A$, $\Sigma B$, $\Sigma C$, and $\Sigma D$ of said voltage maximum and voltage minimum as applied thereto. A second four-input summing circuit 199 receives the signals $\Sigma A$, $\Sigma B$, $\Sigma C$, an $\Sigma D$ from the four second two-input summing circuits 195 to 198 and determines the mean value $\overline{\Sigma}$ of the signals form the four summing circuits 195 to 198. An output amplifier 112 is connected to the output form the summing circuit 199 and delivers a signal to an analog indicator representative of the static force applied by the rotary arm 20 to the stand 23. This signal represents the static load on the stand and may be used, for example, to measure the mass of the specimen mounted in the basket 27.

Two other embodiments of the system for selectively displacing a mass of fluid inside one or more hollow horizontal tubes 25 incorporated in the rotary arm 20 are now described with reference to FIGS. 4 and 5. Like the embodiment of FIG. 1, the embodiments of FIGS. 4 and 5 may use the above-described unbalance detector circuit, and each of them includes a pair of controlling servo-valves 104 (204) controlled by the unbalance measuring circuit and acting in a manner analogous to the servo-valves 4 in the FIG. 1 embodiment. However, in the embodiments of FIGS. 4 and 5, rebalancing is performed solely by displacing a mass of hydraulic fluid and a free piston is no longer used.

In the FIG. 4 embodiment, a pair 106 of flexible membranes 161 and 162 is disposed inside the bore 29 of the hollow tube 25, with the membranes being connected in fluid-tight manner to the side wall of the hollow tube 25 in two radial planes situated at suitable distances from the ends of the bore 29 so as to provide a pair of chambers inside the bore 29 on either side of a central chamber 105 delimited by the two flexible membranes 161 and 162 and the wall of the bore 29. A hydraulic fluid is inserted into the central chamber 105 via an orifice 2. Purge orifices 1 are provided for each of the various compartments defined inside the hollow tube 25.

An air compressor 103 (e.g. up to a pressure of $200 \cdot 10^5$ Pa) or a cylinder of compressed air, is connected via outlet line 17 and return lines 16 to the servo-valves 104 which are themselves connected via lines 15 to the two variable-volume chambers situated between the flexible membranes 161 and 162 and the corresponding ends of the hollow tube 25.

When the unbalance detecting circuit detects an unbalance, signals a and b are applied to the servo-valves 104 in order to apply air under pressure to one or other of the two end chambers in order to take advantage of the flexible membranes 161 and 162 for displacing the mass of liquid situated in the central chamber 105, thereby contributing to rebalancing the rotating arm 20 of the centrifuge in real time.

The embodiment shown in FIG. 5 is analogous to the embodiment shown in FIG. 4 insofar as it uses compressed air to displace a mass of liquid which is used for rebalancing the arm of a centrifuge. However, in FIG. 5, flexible membranes are not used and the hollow tube 25 defines to chambers 261 and 262 which are delimited by fixed walls and which are separated from each other by a fixed transverse wall including the axis of rotation of the turret.

Means 2 are provided through the side wall of the hollow tube 55 for filling one of the chambers, e.g. the chamber 261, with a liquid fluid, and purge means 1 are provided through the bottom wall of each of the chambers 261 and 262. A duct 206 also serves to put the two chambers 261 and 262 into communication with each other. A device 203 for providing compressed air or some other gaseous fluid under pressure is suitable for being selectively connected via servo-valves 204 under the control of the unbalance measuring circuit and via ducts 15 to one or other of the chambers 261 and 262.

FIG. 5 shows the case where the liquid fluid 205 initially in the chamber 261 has been expelled via the duct 206 into the second chamber 262 after compressed air has been applied to the chamber 261 from a compressed air tank 203 via the servo-valve 204 controlled by control signal a delivered by the electronic circuit for measuring unbalance.

Given that the density of the fluids which can be used for this purpose is less than that of a piston made of steel, for example, it is nevertheless generally preferable to obtain rebalancing by making use of the displacement of a hydraulic fluid in combination with the displacement of a solid mass (the free piston 6), as shown in FIG. 1, rather than obtaining dynamic rebalancing solely by means of the mass of the liquid which is displaced.

It may also be observed that the hollow tubes 25 to which the dynamic balancing system of the invention is applied may already exist in the rotary arm of a centrifuge as supporting components, or else they may be added to a rotary arm specifically for the purpose of providing the balancing function. In order to withstand the application of large forces, e.g. during alternating cycles during which large forces are applied in opposite directions to the end of the rotating arm, it is necessary for the bored and lapped hollow tubes 25 to be made of high quality steel. In contrast, the free piston such as the piston 6 shown in FIG. 1, is relatively easy to mount, so a balancing system in accordance with the invention can be fitted to the rotary arms of centrifuges which are already equipped with high quality hollow tubes in a manner which is particularly simple and cheap.

I claim:

1. A system for automatically balancing a centrifuge in operation, the centrifuge including a rotary arm including at least one horizontal tube mounted on a turret for rotation about a vertical axis relative to a stand, the balancing system comprising a system for selectively displacing a mass of fluid inside said hollow horizontal tube, and a circuit for measuring any unbalance of the rotary arm which may be out-of-balance, and the circuit for measuring the unbalance comprising sensors disposed on the centrifuge, circuits for processing the signals delivered by the sensors in order to deliver alarm signals or rebalancing control signals in the event of unbalance being detected, and control means for controlling said system for selectively displacing a mass of fluid, said control means responding to rebalancing control signals delivered by the unbalance measuring circuit in order to give rise to selective real time displacement inside said hollow horizontal tube of a mass of fluid for dynamically rebalancing the rotating arm of the centrifuge.

2. A system for automatically balancing a centrifuge in operation, the centrigue including a rotary arm including at least one horizontal tube mounted on a turret for rotation about a vertical axis relative to a stand, the balancing system comprising a system for selectively displacing a mass of fluid inside said hollow horizontal tube, and a circuit for measuring any unbalance of the rotary arm which may be out-of-balance, and the circuit for measuring the unbalance comprising sensors disposed on the centrifuge, four strain-gauge bridges disposed on elastically deformable parts incorporated in the stand or in the connections between the stand and its foundation, with the four strain gauges lying in a horizontal plane at equal distances from the vertical axis of rotation of the rotary arm and being diametrically opposed in pairs along two mutually orthogonal directions, circuits for processing the signals delivered by the sensors in order to deliver alarm signals or rebalancing controlsignals in the event of unbalance being detected, and control means for controlling said system for selectively displacing a mass of fluid, said control means responding to rebalancing control signals delivered by the unbalnce measuring circuit in order to give rise to selective real time displacement inside said hollow horizontal tube of a mass of fluid for dynamically rebalancing the rotating arm of the centrifuge.

3. A system according to claim 2, wherein the unbalance measuring circuit comprises a signal-shaping circuit for shaping the signals delivered by the strain-gauge bridges, a set of four pairs of sample-and-hold circuits connected so as to store the voltage maxima and the voltage minima delivered by each of the circuits for shaping the signals delivered by the four strain-gauge bridges, four first two-input summing circuits each connected to receive the signals delivered by a pair of the sample-and-hold circuits recording the voltage maximum and the voltage minimum from a respective one of the signal-shaping circuits, each of said summing circuits determining the absolute value of the difference between the voltage maximum and the voltage minimum applied thereto, a first four-input summing circuit connected to receive the signals from said first four two-input summing circuits, and circuits for using the signals delivered by the first four-input summing circuit in order to deliver signals representative of the level of unbalance in the rotating arm to a display member and to members for controlling the system for selectively displacing a mass of fluid inside said hollow horizontal tube in order to reduce the level of unbalance in the rotating arm, when necessary.

4. A system according to claim 3, wherein the unbalance measuring circuit further includes four comparator circuits disposed between the output from the first four-input summing circuit and respective ones of each of the inputs to said first four-input circuit, and wherein the outputs from said comparator circuits are connected to a fault-detection threshold circuit which delivers a signal representative of a fault when the output signal from any one of the comparators exceeds a predetermined value.

5. A system according to claim 3, wherein the unbalance measuring circuit further includes four second two-input summing circuits each connected to receive the signals delivered by a corresponding pair of the sample-and-hold circuits recording the voltage maximum and the voltage minimum from a respective one of the signal-shaping circuits and for determining the sum of said voltage maximum and said voltage minimum, a second four-input summing circuit for receiving the signals from said four second two-input summing circuits and for determining the mean value of the signals from said four second two-input summing circuits, and circuits for using the signal delivered by the second four-input summing circuit in order to deliver a signal representative of the static force exerted on the stand by the rotary arm.

6. A system according to claim 2, wherein the system for selectively displacing a mass of fluid inside said hollow horizontal tube comprises an actuator having a free piston with two transverse end faces delimiting two end chambers inside the hollow cylinder, filling means for filling the empty space situated between the transverse end faces of the free cylinder and the end chambers with oil, an oil tank together with a hydraulic pump, and an oil-removing circuit for removing the oil situated in one or other of the end chambers, said oil-removing circuit being provided with servo-valves under the control of control signals generated by the unbalance measuring circuit.

7. A system according to claim 6, wherein said filling means comprise an oil insertion orifice situated in the middle portion of the hollow horizontal tube in order to insert oil into an annular space lying between the two transverse end faces of the piston, ducts provided in the body of the free piston in order to put said annular space into communication with respective ones of the end chambers, and non-return valves disposed in each of the ducts in order to prevent fluid from returning from the end chambers to said annular space.

8. A system according to claim 2, wherein the system for selectively displacing a mass of fluid inside the hollow horizontal tube comprises a pair of flexible membranes disposed inside the hollow tube and connected in fluid-tight manner to the side wall of the horizontal tube in two radial planes at respective distances from the ends of said tube, means for filling the empty space between the membranes with a liquid fluid, a device for providing a gaseous fluid under pressure, and a selective connection circuit between said device for supplying a gaseous fluid under pressure and each of the variable volume chambers situated between the flexible membranes and the corresponding ends of the hollow tube, said selective connection circuit including servo-valves controlled by control signals delivered by the unbalance measuring circuit.

9. A system according to claim 2, wherein the system for selectively displacing a mass of fluid inside the hollow horizontal tube comprises a first chamber and a second chamber delimited by fixed walls and separated from each other by a fixed transverse wall which inculdes the axis of rotation of the turret, means for filling one of the chambers with a liquid fluid, ducts for putting the two chambers into communication with each other, a device for providing a gaseous fluid under pressure, and a selective connection circuit between the device for providing the gaseous fluid under pressure and each of the chambers, said selective connection circuit including servo-valves controlled by control signals delivered by the unbalance measuring circuit.

10. A system according to claim 8 or claim 9, wherein the gaseous fluid under pressure is compressed air.

11. A system according to claim 6, further including means of a magnetic type for centering the free piston when the centrifuge is stationary.

12. A device according to claim 2, wherein the control of the system for selectively displacing a mass of fluid inside the hollow horizontal tube is capable of being disengaged from the unbalance measuring circuit when the rotary arm of the centrifuge is rotating at a low speed, with the balancing mass being maintained in a neutral position.

13. A system according to claim 2, including a rotary arm constituted by two parallel hollow tubes each fitted with a system for selectively displacing a mass of fluid inside the bore of the corresponding tube, and wherein each of the systems for selectively displacing a mass of fluid is controlled from a common unbalance measuring ciruit.

* * * * *

UNITED STATES PATENT AND TRADEMARK OFFICE
CERTIFICATE OF CORRECTION

PATENT NO. : 4,919,646

DATED : April 24, 1990

INVENTOR(S) : Jacques Perdriat

It is certified that error appears in the above-identified patent and that said Letters Patent is hereby corrected as shown below:

Column 1 Line 6 "centrigue" should read --centrifuge-- (second occurrence).

Column 1 Line 63 after "signals" insert --delivered by the sensors in order to deliver alarm signals--.

Column 1 Line 66 "contorl" should read --control--.
Column 3 Line 40 "and" should read --to--.
Column 3 Line 41 "form" should read --from--.

Column 4 Line 23 "psace" should read --space--.

Column 4 Line 35 "is" should read --it--.

Column 6 Line 55 "- $\Delta$-R" should read -- - $\Delta R$--.

Column 7 Line 10 "$(-I_{AM}$" should read --$(-U_{AM}$--.

Column 7 Line 10 after ")" insert -- 1 --.

UNITED STATES PATENT AND TRADEMARK OFFICE
CERTIFICATE OF CORRECTION

PATENT NO. : 4,919,646

DATED : April 24, 1990

INVENTOR(S) : Jacques Perdriat

Page 2 of 3

It is certified that error appears in the above-identified patent and that said Letters Patent is hereby corrected as shown below:

Column 7 Line 23 "form" should read --from--.

Column 7 Line 35 "81, 85;" should read --91, 95;--.

Column 7 Line 59 "193" should read --194--.

Column 8 Line 10 "form" should read --from--.

Column 8 Line 21 "and" should read --to--.

Column 8 Line 24 "form" should read --from--.

Column 8 Line 47 "$U_{AM}$" (second occurrence) should read --$U_{Am}$--.

Column 8 Line 52 "an" should read --and--.

UNITED STATES PATENT AND TRADEMARK OFFICE
CERTIFICATE OF CORRECTION

PATENT NO. : 4,919,646

DATED : April 24, 1990

INVENTOR(S) : Jacques Perdriat

It is certified that error appears in the above-identified patent and that said Letters Patent is hereby corrected as shown below:

Column 8 Line 54 "form" should read --from--.

Column 8 Line 56 "form" should read --from--.

Claim 2 Line 58 Column 10 "controlsignals" should read --control signals--.

Claim 2 Line 62 Column 10 "unbalnce" should read --unbalance--.

Claim 7 Line 4 Column 12 after "between" insert --the free piston and the bore of the hollow tube between--.

Claim 9 Lines 31-32 Column 12 "inculdes" should read --includes--.

Signed and Sealed this

Seventeenth Day of September, 1991

*Attest:*

HARRY F. MANBECK, JR.

*Attesting Officer*  *Commissioner of Patents and Trademarks*